United States Patent [19]

Senni et al.

[11] 4,293,494
[45] Oct. 6, 1981

[54] METHOD FOR THE PURIFICATION OF RAW CAPROLACTAM WHICH CONTAINS AMIDES AND OTHER BY-PRODUCTS

[75] Inventors: Paolo Senni, Colleferro; Domenico Astarita, Segni, both of Italy

[73] Assignee: Snia Viscosa S.p.A., Milan, Italy

[21] Appl. No.: 143,418

[22] Filed: Apr. 24, 1980

[30] Foreign Application Priority Data

May 4, 1979 [IT] Italy ............................... 22355 A/79

[51] Int. Cl.³ .......................................... C07D 201/16
[52] U.S. Cl. .............................................. 260/239.3 A
[58] Field of Search ................................. 260/239.3 A

[56] References Cited

U.S. PATENT DOCUMENTS 2,758,991  8/1956  Kretzers et al. ............. 260/239.3 A

*Primary Examiner*—Robert T. Bond
*Attorney, Agent, or Firm*—Hubbell, Cohen, Stiefel & Gross

[57] ABSTRACT

A method for purifying raw caprolactam containing, as impurities, primary amides of the formula $$R-\overset{O}{\underset{\|}{C}}-NH_2 \qquad (I)$$

R being a hydrocarbon radical having 1–14 carbon atoms, and other by-products is described. The operations, carried out in the following order, consist in (a) treating a solution of raw caprolactam in a water insoluble organic solvent with water to extract most of the caprolactam in purified form, (b) separating the aqueous caprolactam solution and isolating the caprolactam, (c) treating the remaining organic solution with mineral acid to cause the formation of two phases, (d) separating these phases into a heavy phase containing the mineral acid, dilution water and most of the amides and by-products and a light phase containing the organic solvent and any residual amides and by-products, and (e) preferably recycling the light phase to (a). Further object of the invention is the purified caprolactam thus obtained.

9 Claims, No Drawings

METHOD FOR THE PURIFICATION OF RAW CAPROLACTAM WHICH CONTAINS AMIDES AND OTHER BY-PRODUCTS

BACKGROUND OF INVENTION

The present invention relates to a method for the purification of raw caprolactam which contains as impurities primary amides according to general formula I

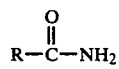

$$R-\overset{O}{\underset{\|}{C}}-NH_2 \quad (I)$$

wherein R is a hydrocarbon radical having from 1 to 14 carbon atoms, in particular hexahydrobenzamide, and other by-products. The present invention further refers to the caprolactam thus purified.

Methods for the purification of the raw caprolactam which contains amides as hereinbefore defined, in particular hexahydrobenzamide and other by-products, are known. Said methods may be grouped in two different classes, and in particular, they may be classed as methods having a chemical nature and methods having a physical nature. Thus e.g. a method having a chemical nature is claimed in the Japanese patent application No. 46-23751, said method being characterized by the fact that raw caprolactam is treated with a sodium hypochlorite solution. Another method having a chemical nature is claimed in DOS No. 1.926.932 and consists in treating the molten raw caprolactam with metal oxides. The methods having a physical nature mainly consist in distilling and/or rectifying the caprolactam. Thus e.g. in English Pat. No. 1,157,416 a method for the purification of caprolactam by distillation is described. In Italian patent application No. 20612 A/79 of the Applicant a method for the purification of raw caprolactam by a combination of distillation and rectification operations is described and claimed.

This last method described in patent application No. 20612 A/79 of the Applicant, while it permits one to obtain the greater part of the caprolactam in such a pure form that it may be employed industrially to make polycaprolactam, has however the drawback that rectification or distillation tails, which contain, besides one or more amides as hereinbefore defined and other by-products, also considerable amounts of caprolactam must be discarded. In order to render the process economical it is necessary to recover said caprolactam from the rectification tails.

FIELD OF THE INVENTION

The Applicant has now surprisingly found a method for purifying raw caprolactam which contains one or more amides as hereinbefore defined, in particular hexahydrobenzamide, and other by-products, by which the aforesaid disadvantages are pratically eliminated.

SUMMARY OF THE INVENTION

The present invention, provides a method for eliminating the hereinbefore defined amide or amides from said rectification or distillation tails and therefore for recovering the caprolactam contained in said rectification tails. Said rectification or distillation tails may be treated alone, as it is preferable to do in a discontinuous process, or they may be treated together with the lactam oil, as it is preferable to do in a continuous process.

The present method is characterized by the fact that the aforesaid impurities are separated from the caprolactam by a series of extractions with selective solvents.

The method according to the invention herein described is conveniently used when the caprolactam obtained e.g. from the nitrosation of hexahydrobenzoic acid is extracted from its sulphuric solutions after neutralizing the same, e.g. with ammonia, and extracting with an aromatic hydrocarbon, e.g. toluene.

By said method it is possible to treat caprolactam which originates from caprolactam distillation and/or rectification operations, operations from which there are obtained, on the one hand, mostly pure caprolactam and, on the other hand, (e.g. as a residue of the distillation and of rectification) a caprolactam in which the content of amide impurities has been considerably increased to ten times their initial value. Said impure lactam, once it has undergone the treatment for the partial or total elimination of the amides according to the present invention, may go back into the purification cycle described in the Italian patent application of the Applicant No. 20612 A/79.

Italian patent application No. 20612 A/79 contains the following disclosure:

"This invention relates to a method of purifying caprolactam, e.g., caprolactam of the same grade as yielded by reacting nitrosyl compounds with carbocyclic derivatives."

It is a well known fact that the aforesaid reaction yields additionally to caprolactam, small amounts of non-cyclic amides, such as acetamide, propionamide, butyramide n-valeramide, benzamide, tetrahydrobenzamide, hexahydrobenzamide, and moreover, still in small amounts, aliphatic and aromatic cyclocarboxylic acids, epsilon-aminocapronic acid, and unsaturated oxidable substances.

Several methods of purifying caprolactam are known in the art. Thus, for example, when effectuated by reacting nitrosyl compounds with carbocyclic derivatives, the purification of caprolactam (following its extraction from the sulphuric reaction mass and known steps for separating raw caprolactam) is substantially carried out, according to current practice, by means of two separate and discrete chemical treatments, a first one directed to destroying the amides, and a second one directed to reducing or eliminating the easily oxidable substances. More specifically, these treatments consist of subjecting firstly the raw caprolactam to the action of sodium hypochlorite (conversion of the amides into more volatile amines), and subsequently to an oxidizing action, e.g. with potassium permanganate or ozone (decomposition of the oxidable substances); the product, after undergoing that treatment, is subjected to distillations, possibly under vacuum conditions, without rectification, thereby a "polymerization grade" caprolactam is obtained. Said chemical treatments, however, have the following drawbacks:

(1) they are expensive;
(2) they yield impurities of a different nature (such as chloro-lactams, for instance) which, although only some ppm, result in contamination of the caprolactam;
(3) the treatments with hypochlorite-permanganate, respectively hypochlorite-ozone, are not absolutely selective, even when the very high caprolactam by-products ratio is taken into account, thereby part of the caprolactam is destroyed by these chemicals, with an attendant appreciable decrease of the yield.

The Applicant has now surprisingly found a method of purifying caprolactam by the application of only one line of physical purification. With this process it becomes possible to obtain a caprolactam of a purity even higher than that obtainable with the use of hypochlorite-permanganate, respectively, hypochlorite-ozone.

By not applying said treatments of a chemical nature, not only all of the aforesaid disadvantages are eliminated, but a lower cost and improved environmental protection can also be achieved in the purification process.

This invention sets out to provide a caprolactam purification process by vacuum distillation, characterized in that said distillation is carried out, in a continuous and/or discontinuous (batch distillation) manner, in the following stages or steps, in the same order as listed herebelow:

(a) fast vacuum distillation of the raw caprolactam, possibly in the presence of an alkaline and/or alkaline-earth hydroxide;

(b) distillation with vacuum rectification of the caprolactam yielded as distillate from (a), with separation from the high-boiling, and possibly low-boiling, by-products; and (c) fast vacuum distillation of the caprolactam yielded from (b), in the presence of an alkaline and/or alkaline-earth hydroxide.

The term "fast distillation", as used herein, is intended to describe an operation wherein the evaporated material is no more recycled, in any substantial manner, into the evaporation zone. The percentage by weight of the alkaline or alkaline-earth hydroxide, at step (c), and possibly (a) as well, with respect to caprolactam, varies preferably in the 0.05% to 5% range, and more preferably from 0.1% to 1.0%.

Advantageously, the temperature of the various steps (a), (b) and (c) are preferably maintained within the following limits:

Step (a)—100° to 150° C.
Step (b)—vapors, 110° to 150° C.; reboiler, 120° to 180° C.;
Step (c)—100° to 150° C.

As the alkaline hydroxide, potassium hydroxide is used of preference, and more preferably sodium hydroxide, whereas when an alkaline-earth hydroxide is used, calcium hydroxide is preferred; however, as the hydroxide, according to this invention, sodium hydroxide is still more preferably employed. Said alkaline or alkaline-earth hydroxides are preferably employed, in accordance with this invention, in the form of a solution, and more preferably of an aqueous solution.

According to a variant of the invention, (mainly suggested by economics and physical-mechanical considerations) the purification of caprolactam is carried out at the steps (a), (b) and (c) such as to obtain:

From Step (a), a distilled portion corresponding to 90-98% by weight with respect to the raw caprolactam and 2-10% by weight of residue, again with respect to the raw caprolactam;

from Step (b), a head fraction, corresponding to 2-5% by weight with respect to the caprolactam supplied from Step (a), a core fraction, corresponding approximately to 90% by weight of the caprolactam supplied from Step (a), and a residue corresponding to 5-8% by weight again with respect to the caprolactam supplied from Step (a);

from Step (c), a fast distillate to yield a residue corresponding to approximately 5-10% by weight of the caprolactam supplied from Step (b).

In step (b), the head fraction may or may not be separated from the caprolactam which is supplied to the successive step (c).

The operating conditions which can be adopted for the two fast distillations, as per steps (a) and (c), are the following:

Temperatures in the 125° to 130° C. range;
Residual pressure, 4 mm Hg;

and for the rectification of step (b):

Head temperatures in the 105° to 110° range;
Reboiler temperature in the 120° to 165° C. range.

The finally yielded caprolactam has the following characteristics:

Volatile bases, 0.1 meq/kg;
Permanganate Number, 15,000 seconds;
HAZEN color, less than 5;
Absorption at 290 nm, 0.008;
Absorption summation from 260 to 300 nm, 0.290.

None of the individual operations, when carried out separately and/or in a different order from the one provided by the invention, yields caprolactam having the aforesaid characteristics.

A further object of this invention includes the purified caprolactam as obtained with the purification method described hereinabove.

The following example should be considered as merely illustrative and in no way limitative of this invention.

EXAMPLE

Step (a)

Into a glass flask equipped with thermometer, capillary tube for the introduction of nitrogen, vapor collecting and condensing system, vacuum unit, and vacuum measuring gauges, as well as outer electric heater, there are charged 100 parts by weight of raw caprolactam and 0.3 parts by weight of NaOH, as a 50% solution in $H_2O$. The flask is heated up to 110° C. at a residual pressure of 1.2 mm Hg. The results are shown in the following Table 1.

TABLE 1

| CHARGE | 100 parts by weight |
|---|---|
| Total volatile bases charged | 24.3 meq/kg |
| Volatile bases charged as hexahydrobenzamide (HBA) | 17.8 meq/kg |
| Permanganate Number | 0 seconds |
| DISTILLATE | 80 parts by weight |
| Total volatile bases | 10.2 meq/kg |
| HBA volatile bases | 7.4 meq/kg |
| Permanganate Number | 150 seconds |
| TAILS | 20 parts by weight |
| Total volatile basis | 80.7 meq/kg |
| HBA volatile basis | 59.4 meq/kg |
| Permanganate Number | 0 seconds |
| Oligomers | none |

Step (b)

The apparatus utilized to carry out step (b) comprises a glass flask equipped with capillary tube for the introduction of nitrogen, thermometer, pressure gauge for measuring the vacuum, and outer electric heater system. Over the flask, there is mounted a 20-plate rectification column which is connected to a reflux head and then to an overall condenser discharging into a distillate collection flask whereto a vacuum is applied. Into the heated flask, are charged 80 parts by weight of the caprolactam from the distillate of step (a); heat is applied after a 3 mm Hg vacuum has been created in the collecting flask (in the boiler the vacuum is of 25 mm Hg). Before the collection is initiated, the caprolactam is fully recycled to ensure that the column operating conditons are achieved. Then, 4 parts by weight of caprolactam are distilled, collected and separated at the head temperature of 124° C., and 64 parts by weight of caprolactam are collected and separated at the temperature of 125° C. Distillation is then discontinued, and in the boiler there remain 12 parts by weight of caprolactam. The results obtained are tabulated in the following Table 2.

TABLE 2

| CHARGE | 80 parts by weight |
|---|---|
| RECTIFICATION HEADS | 4 parts by weight |
| Total volatile bases | 1.78 meq/kg |
| HBA volatile bases | none |
| Permanganate Number | 0 seconds |
| RECIFICATION TAILS | 12 parts by weight |
| Total volatile bases | 66.5 meq/kg |
| HBA volatile bases | 49.3 meq/kg |
| Permanganate Number | 0 seconds |
| Oligomers | none |
| RECTIFICATION CORE | 64 parts by weight |
| Total volatile bases | 0.17 meq/kg |
| HBA volatile bases | none |
| Permanganate Number | 3800 seconds |

Step (c)

The apparatus employed to carry out this step is the same as for step (a). There are charged into it 64 parts by weight of caprolactam from the rectification core (step (b)) and 0.15 parts by weight of NaOH as a 50% solution in $H_2O$. One proceeds as in step (a), and the results are tabulated in the following Table 3.

TABLE 3

| CHARGE | 64 parts by weight |
|---|---|
| TAILS | 6.4 parts by weight |
| Total volatile bases | 0.76 meq/kg |
| Permanganate Number | 0 seconds |
| Oligomers | none |
| DISTILLATE | 57.6 parts by weight |
| Total volatile bases | 0.04 meq/kg |
| HBA volatile bases | none |
| Permanganate Number | 15,000 |
| Absorption at 290 nm | 0.008 ".— |

An object of the present invention is therefore a method for the purification of raw caprolactam, which contains as impurities one or more amides as hereinbefore defined and other by-products, charaterized by the fact that the following operations are carried out in the order hereinbelow indicated:

(a) a solution of raw caprolactam in an organic solvent, which is substantially insoluble in water, is treated with water so as to extract the greater part of the caprolactam in purified form;

(b) the aqueous caprolactam solution is separated and the caprolactam is isolated by known methods;

(c) the remaining solution in the organic solvent, which contains a portion of the amides and of the by-products, is treated with a mineral acid in such a concentration as to be inert with respect to organic solvent and to cause the formation of two separate phases;

(d) the two phases of the mixture which have been formed are separated into a heavy phase, which contains the mineral acid, its respective dilution water and the greater part or all the amides according to formula I and the other aforesaid by-products; and a light phase, which contains said organic solvent and any eventual amount of residual amides and by-products.

(e) said light phase is in general and preferably recycled to stage (a) by known methods.

DETAILED DESCRIPTION OF THE PREFERRED EMBODIMENTS

Preferably sulphuric acid having a concentration of $H_2SO_4$ from 50 to 90% by weight is employed as mineral acid for carrying out the purification of the organic solvent.

The amount of mineral acid employed in the stage (c) is from 0.02 to 0.2 parts by weight per part of raw caprolactam.

As an organic solvent practically insoluble in water, e.g., benzene, toluene, ortho-, meta-, para-xylene or their mixture, preferably toluene, may be employed.

According to the present invention the concentration of raw caprolactam in the organic solvent substantially insoluble in water, is comprised from 2 to 12% preferably from 3 to 10% by weight. If toluene is employed as the organic solvent, said concentration is about 10% by weight.

Conveniently, according to the present invention, the water is added to the solution of raw caprolactam in the organic solvent, in an amount preferably comprised between 20 and 150% by weight with respect to the raw caprolactam.

Preferably the operations indicated at stages (a), (c) and (d) hereinbefore described, are effected at a temperature. comprised between 15° and 25° C., preferably at room temperature.

A further object of the present invention is the caprolactam purified by the method hereinbefore specified.

The following examples are illustrative and are not intended to limit the present invention in any way.

EXAMPLE N. 1

An apparatus consisting of two machanically stirred extraction columns and a glass vessel comprising a stirring or agitated zone and a decantation zone is used for the treatment of the toluene solution with sulphuric acid.

The purification test is effected in the following way: (The temperatures of the several parts of apparatus and the pressures are room temperatures and pressures; meq signifies milli-equivalents).

495 g/h of raw lactam oil treated with soda corresponding to 200 g/h of pure caprolactam and meq/h of amides of the formula I are fed continuously to the top of a column (C-1).1700 g/h of toluene coming from the RTS vessel (reactor for the treatment of discharge toluene) are fed to the base of said column (C-1).

A solution of caprolactam in toluene, which has the following composition by weight: toluene about 90%, caprolactam about 10%, exits from the top of column (C-1) and enters at the base of column (C-2).

200 g/h of water are fed to the top of column (C-2) while 400 g/h of 50% caprolactam aqueous solution, having a content of amides of formula I of 5.6 meq/h, are discharged from the bottom of the same. About 1700 g/h of raw toluene having a total content of amides of formula I of 3.6 meq/h flow out of the top of column (C-2). Toluene enters in RTS where 14 g/h of 82% H₂SO₄ are concurrently fed. The content of amides of formula I in the toluene which flows out of RTS is pratically zero; said toluene enters directly at the bottom of column (C-1). Sulphuric acid flows out of RTS with a content of amides of formula I of 3.6 meq/h. The balance of the amides having the formula I shows that 40% of the amides fed to column (C-1) together with the caprolactam are discharged with the sulphuric acid.

We claim:

1. A method for the purification of raw caprolactam, which contains as impurities one or more primary amides according to formula I:

wherein R is a hydrocarbon radical having from 1 to 14 carbon atoms, and other by-products, comprising performing the following operations in the order indicated hereinbelow:

(a) treating a solution of said raw caprolactam in which the solvent is a substantially water insoluble organic solvent with water in such a way as to extract the greater part of the caprolactam in purified form;

(b) separating the aqueous caprolactam solution from the water insoluble organic solvent and isolating the caprolactam from the aqueous solution;

(c) treating the remaining solution containing the organic solvent with a mineral acid in a concentration as to be inert with respect to the organic solvent and to cause the formation of two separate phases;

(d) separating the two phases into a heavy phase, containing the mineral acid, its respective dilution water and the greater part or all the amides according to formula I and said by-products; and a light phase containing said organic solvent; and (e) recycling said light phase to (a).

2. A method according to claim 1, wherein the amide according to formula I is hexahydrobenzamide.

3. A method according to any one of claims 1 or 2, wherein the organic solvent employed is toluene and the mineral acid, is sulphuric acid having an H₂SO₄ concentration from 50 to 90% by weight.

4. A method according to claim 3, wherein the mineral acid of claim 1 is employed in an amount between 0.02 and 0.2 parts by weight of raw caprolactam.

5. A method according to claim 4, wherein the concentration of raw caprolactam in the organic solution, is between 2 and 12 percent by weight.

6. A method according to claim 5, wherein the concentration of raw caprolactam in toluene is approximately 10 percent by weight.

7. A method according to claim 5, wherein the amount of water added to the raw caprolactam solution is between 20% and 150% by weight with respect to the raw caprolactam.

8. A method according to claim 4 further comprising that the operations referred to as stages (a), (c) and (d) are carried out at a temperature of between 15° and 25° C.

9. The method of claim 5, wherein the concentration of raw caprolactam in the organic solvent solution is from 3 to 10% by weight.

* * * * *

UNITED STATES PATENT OFFICE
CERTIFICATE OF CORRECTION

Patent No. 4,293,494    Dated Oct. 6, 1981

Inventor(s) PAOLO SENNI, et al

It is certified that error appears in the above-identified patent and that said Letters Patent are hereby corrected as shown below:

Column 1, line 60: "pratically" should read --practically--

Column 2, line 30: delete the quotation mark (")

Column 5, line 48: after the quotation mark (") delete

".—"

Column 5, line 9: "conditons" should read --conditions--

Column 6, line 36: after "ature" delete the period (.)

Column 7, line 4: "pratically" should read --practically--

Signed and Sealed this

Fifth Day of October 1982

[SEAL]

Attest:

GERALD J. MOSSINGHOFF

Attesting Officer    Commissioner of Patents and Trademarks